United States Patent [19]

Klein et al.

[11] Patent Number: 5,233,997
[45] Date of Patent: Aug. 10, 1993

[54] NON-INVASIVE MEASURE OF INTESTINAL TRANSIT TIME AND USES THEREOF

[75] Inventors: Peter D. Klein, Houston, Tex.; Willi E. K. Heine, Rostock; Heiner K. Berthold, Heidelberg, both of Fed. Rep. of Germany

[73] Assignee: Baylor College of Medicine, Houston, Tex.

[21] Appl. No.: 680,483

[22] Filed: Apr. 4, 1991

[51] Int. Cl.[5] ............................................. A61B 5/08
[52] U.S. Cl. .................................. 128/718; 128/654; 128/898; 600/3; 424/9
[58] Field of Search ........ 128/654, 898, 716, 718–720; 600/3–5; 604/49; 424/2, 9

[56] References Cited

U.S. PATENT DOCUMENTS

| | | | |
|---|---|---|---|
| 3,852,413 | 12/1974 | Cammarata | 424/9 |
| 4,171,352 | 10/1979 | Wolgemuth et al. | 424/9 |
| 4,203,967 | 5/1980 | Gallo-Torres | 424/9 |
| 4,351,823 | 9/1982 | Rubin | 424/9 |
| 4,382,887 | 5/1983 | Shibata | 424/9 |
| 4,670,245 | 6/1987 | Vasquez et al. | 424/9 |
| 4,676,974 | 6/1987 | Hofmann et al. | 424/9 |

FOREIGN PATENT DOCUMENTS

| | | |
|---|---|---|
| 1037768 | 9/1978 | Canada |
| 161987 | 9/1983 | Japan |

OTHER PUBLICATIONS

"The nitrogen value of lactosylurea for ruminants."; Grenet et al. 1983. (abstract only).

"Synthesis of microbial nitrogen compounds in the rumen and their digestion in the small intestine"; Smith et al. 1976. (abstract only).

King, C. E. and Toskes, P. P. Comparison of the 1--Gram [$^{14}$C]Xylose, 10-Gram Lactulose-$H_2$, and 80--Gram Glucose-$H_2$ Breath tests in patients with small intestine bacterial overgrowth. Gastroenterology 1986;91:1447-51.

Devroede, G. and Soffie, M. Colonic absorption in idiopathic constipation. Gastroenterology 1973;64:553-561.

Waller, S. L. Differential measurement of small and large bowel transit times in constipation and diarrhea: A new approach, Gut. 1975;16:372-378.

King C. E., et al. Detection of small intestine bacterial overgrowth by means of a $^{14}$C-D-Xylose Breath Test, Gastroenterology 1979;77:75-82.

Arhan, P., et al. Segmental Colonic Transit Time*. Dis. Colon Rectum 1981;24:624-629.

Corazza, G. R., et al. The diagnosis of small bowel bacterial overgrowth; Reliability of jejunal culture and inadequacy of breath hydrogen testing. Gastroenterology 1990;98:302-309.

Read, N. W., et al. Transit of a meal through the stomach, small intestine, and colon in normal subjects and its role in the pathogenesis of diarrhea. Gastroenterology 1980;79:1276-1282.

Everhart, J. E. and Renault, P. F. Irritable bowel syndrome in office-based practice in the United States. Gastroenterology 1991;100:998-1005.

James, W. B. and Hume, R. Action of metoclopramide on gastric emptying and small bowel transit time. Gut. 1968;9:203-205.

Hanson, C. F. and Winterfeldt, E. A. Dietary fiber effects on passage rate and breath hydrogen. The American Journal of Clinical Nutrition 1985;42:44-48.

Kaufman, P. N., et al. Role of opiate receptors in the (List continued on next page.)

Primary Examiner—John D. Yasko
Assistant Examiner—Chalin Smith
Attorney, Agent, or Firm—Fulbright & Jaworski

[57] ABSTRACT

A measurement test for gastrointestinal transit time, including the steps of administering a dose of labeled glycosyl ureide, measuring the labeled $CO_2$ and determining the amount of $CO_2$ over time is described. The assay can be used for measuring the effectiveness of drugs, the effect of drugs on gastrointestinal motility diagnoses of gastrointestinal motility disease measuring the effectiveness of treatment, and the effect of diet on motility.

11 Claims, 8 Drawing Sheets

OTHER PUBLICATIONS regulation of colonic transit. Gastroenterology 1988;94:1351-6.

Piccione, P. R., et al. Intestinal dysmotility syndromes in the elderly: Measurement of orocecal transit time. Am. J. Gastroent 1990;85(2):161-164.

Preston, D. M., et al. Letters to the editor; Naloxone in chronic constipation. Lancet Apr. 2, 1983:758.

Wald, A., et al. Gastrointestinal transit: The effect of the menstrual cycle. Gastroenterology 1981;80:1497-1500.

Kerlin, P. and Wong, L. Breath hydrogen testing in bacterial overgrowth of the small intestine. Gastroenterology 1988;95:982-8.

Rhodes, J. M., et al. The lactulose hydrogen breath test as a diagnostic test for small-bowel bacterial overgrowth. Scand. J. Gastroent, 1979;14:333-336.

Donaldson, R., Jr. and Toskes, P. P. The relation of enteric bacterial populations to gastrointestinal function and disease. Chapter 5 in *Gastrointestinal Diseases*, 5th edition, Fortran & Schlesinger (eds.), W. B. Saunders Co., Phila. 1990.

Cohen, S. and Snape, W. J., Jr. Movement of small and large intestine. Chapter 58 in *Gastrointestinal Diseases*, 5th edition, Fortran & Schlesinger (eds.), W. B. Saunders Co., Phila. 1990.

Kaufman, P. N., et al. Effects of liquid versus solid diet on colonic transit in humans; Evaluation by standard colonic transit scintigraphy. Gastroenterology 1990:98:73-81.

NON-INVASIVE MEASURE OF INTESTINAL TRANSIT TIME AND USES THEREOF

FIELD OF THE INVENTION

This invention relates to methods of measuring intestinal transit time. More particularly, it relates to diagnosing and monitoring the treatment of motility disorders in the gastrointestinal tract.

BACKGROUND OF THE INVENTION

Current non-invasive tests to measure intestinal transit time or detect bacterial overgrowth are largely based on the use of substrates (e.g., $^{14}C$-xylose) which are either almost exclusively metabolized by bacteria or are malabsorbed and subsequently split by colonic bacteria, e.g., $^{14}C$-glycocholic acid. Isotopically labeled $CO_2$ or unlabeled metabolites (e.g., $H_2$) that result from the bacterial degradation of substrates of this type may then be absorbed, transported by the circulation, and finally exhaled by the lungs. Typical tests based on this concept are the $^{13}C$-urea breath test and the lactulose-hydrogen breath test. The reliability of these tests, however, may be limited by irregularities in gastric emptying, rapid absorption and renal excretion of the substrates, intestinal recycling, and intermediary metabolism. Consequently, there is a need for tracer substances which are characterized by minimal absorption and endogenous degradation, but which are acted upon by specific bacterial enzymes that bring about the release, absorption, and exhalation of labeled volatile metabolites. In addition, the extension of the benefits of breath test analysis to studies of infants and children, and women of reproductive age demands the development of nonradioactive alternatives to $^{14}CO_2$ tests that are currently used.

Estimates of transit time in the gastrointestinal tract depend upon: (1) the time for initial or peak appearance of hydrogen in breath from the bacterial fermentation of a non-absorbable sugar, for example, lactulose; (2) the appearance of chromium oxide or styrofoam markers in the stool; or (3) the fluoroscopic examination of the passage of radio-opaque markers through the intestinal tract.

These measurements are inaccurate and/or burdensome. For example, breath hydrogen measurements are inaccurate and not reflective of true mouth to colon transit times. In addition, there are "non-responders" to the $H_2$ breath test in the normal population. Ingestion of stool markers requires collection and examination of the stool and limits the number of studies that can be performed on the same individual over a short period of time. Fluoroscopic examinations present a radiation hazard. These inaccuracies and burdens are significantly reduced or absent in the procedure of the present invention. Further, the present procedure offers numerical characterization of transit processes that are independent of observer judgment.

Glycosyl ureides are condensation products of reducing sugars and urea. They were first described in 1903 and their chemical and physiological properties have since been repeatedly studied. In the glycosyl ureides, the molecular linkage between the carbohydrate and the urea has been shown to resist cleavage by gastrointestinal enzymes, but is capable of being split by colonic flora. The resistance of the glycosyl ureide bond to enzymatic cleavage was noted as early as 1931 using glucose ureide as a model. Most of the microbes tested in vitro failed to release glucose from glucose ureide. Selected putrefactive bacteria, however, were shown to decompose glucose ureide to ammonia. Further, urease from soybeans does not split glycosyl-bound urea. Nevertheless, as shown in the present invention, enzymatic cleavage of monosaccharide units from disaccharide ureides does not seem to be difficult for intestinal and bacterial enzymes. Glycosyl ureides apparently are partially absorbed but undergo no appreciable metabolism. Although many of the chemical and physiological properties of the glycosyl ureides are known, until the present invention, there has been no use of, or suggestion of use of, the glycosyl ureides (1) to measure gastrointestinal motility, (2) to monitor treatment, (3) to diagnose disease, or (4) to monitor drug transit in the gastrointestinal tract.

A primary basis for using the $^{13}C$-labeled glycosyl ureides of the present invention as markers for the bacterial colonization of the intestine is their poor absorption. High absorption rates would prevent these substrates from reaching the terminal ileum, where bacterial colonization starts in normal man, and thus no knowledge would be gained on intestinal transit time. If early bacterial degradation products are formed and absorbed, however, their excretion could indicate bacterial overgrowth.

SUMMARY OF THE INVENTION

An object of the present invention is a non-invasive method for measuring gastrointestinal tract transit time.

An additional object of the present invention is a method for diagnosing motility disease in the gastrointestinal tract.

A further object of the present invention is a method for monitoring the effectiveness of treatment of intestinal motility disease.

An additional object of the present invention is a method for measuring the effect of drugs or diet on gastrointestinal tract motility.

Another object of the present invention is an accurate measurement of drug transit time in the gastrointestinal tract.

Thus, in accomplishing the foregoing objects, there is provided in accordance with one aspect of the present invention a non-invasive method for determining intestinal transit time comprising the steps of administering an oral testing dose of labeled glycosyl ureide to a subject to the tested, sampling respiratory gas over time from the subject, and measuring the amount of labeled $CO_2$ in the respiratory gas.

In alternate embodiments of the invention, the labeled glycosyl ureide is selected from the group consisting of lactose-$^{13}C$-ureide, cellobiose-$^{13}C$-ureide and 1-$^{13}C$-lactose ureide.

Another embodiment of the present method involves monitoring the effectiveness of treatment of intestinal motility disease comprising the steps of first measuring the transit time by administering an oral dose of labeled glycosyl ureide to a subject to be tested, collecting respiratory gas over time from the subject, measuring the amount of labeled $CO_2$ in the respiratory gas, then administering the treatment, and finally remeasuring the transit time. This later procedure is also useful in measuring the effect of drugs on gastrointestinal tract motility.

Other and further objects, features and advantages will be apparent and more readily understood from a reading of the following specification by reference to the accompanying drawings, forming a part thereof, where examples of the presently preferred embodiments of the invention are given for the purpose of disclosure.

DETAILED DESCRIPTION

It will be readily apparent to one skilled in the art that various substitutions and modifications may be made to the invention disclosed herein without departing from the scope and spirit of the invention.

Figure 1:
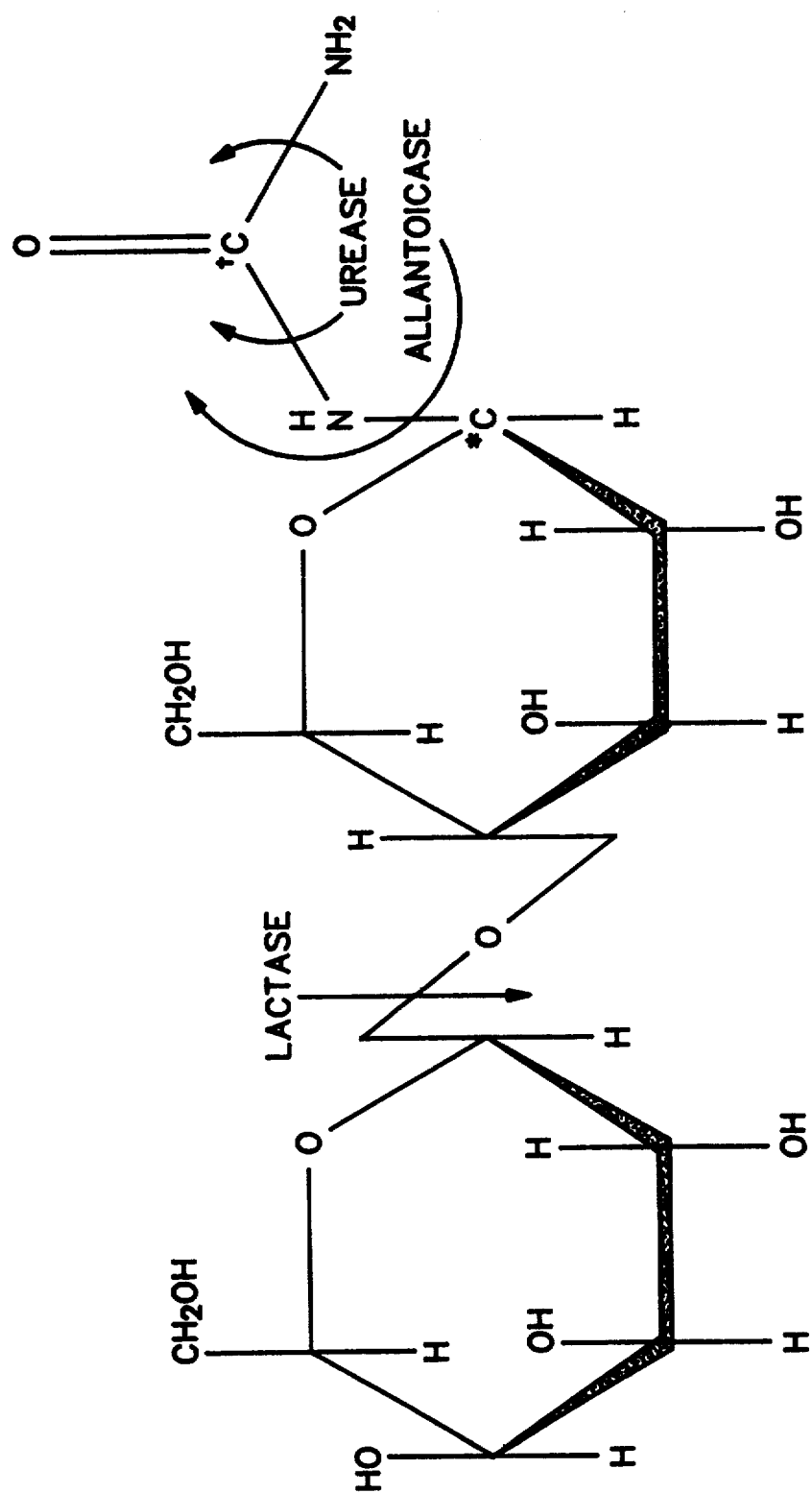
FIG. 1 shows the molecular structure of lactose ureide. The * and the + represent the positions of $^{13}C$ in the 1-$^{13}C$-lactose ureide and lactose-$^{13}C$-ureide, respectively. Suspected degradative enzymes and their sites of cleavage are represented.

The term "labeled" compound as used herein represents that a variety of the elemental atoms of the glycosyl ureides can be labeled. One skilled in the art understands that isotopes of carbon, nitrogen, oxygen and hydrogen can be used. In the preferred embodiment the non-radioactive $^{13}C$ is used. The specific location of the label is shown in FIG. 1 by an * or a +.

In the preferred embodiment, the useful $^{13}C$ glycosyl ureides used include lactose-$^{13}C$-ureide, cellobiose-$^{13}C$-ureide and 1-$^{13}C$-lactose ureide.

As used herein "xenolytic activity" means enzyme activity found in the gastrointestinal tract which depends on the substrate encountering foreign enzyme activity, usually bacterial enzymes of the physiological flora.

The non-invasive transit time measurement of the present invention measures the time it takes for the glycosyl ureide to reach the area of bacterial colonization. This time until peak excretion of label is a measure of the time required to transit from the mouth to the transverse colon. It integrates the gastric emptying and is not sensitive to the length of time it take gastric emptying nor the much shorter time which can be measured by lactulose which is mouth to ileal cecal valve measurement. The time is approximately 6 to 7 hours in normal individuals.

Because the label is essentially removed from the subject's body within 15 hours the transit time can be measured daily. This is a significant improvement over currently used tests.

The present invention is a non-invasive method for determining intestinal transit time comprising the steps of administering an oral testing dose of labeled glycosyl ureide to a subject to be tested, sampling respiratory gas over time from said subject and measuring the amount of labeled $CO_2$ in said respiratory gas.

The testing dose of labeled glycosyl ureide which is administered as a bolus to the subject to be tested, is in the range of 10 to 20 mg/kg. This is a testing dose equivalent to 1 to 5 mg/kg of urea administered orally. In the preferred embodiment, a testing dose equivalent to 2.5 mg/kg of urea is administered orally.

Alternate embodiments of the invention include a method of diagnosing intestinal motility diseases. In this method, the intestinal time is determined as described above and the resultant time is compared with the transit time seen in normal individuals. Individuals with hypermotility or hypomotility can be determined with this procedure.

Some examples of disease states and/or symptoms and/or specific mechanisms which can be diagnosed with the present invention include scleroderma, neuronal type of chronic idiopathic intestinal pseudo-obstruction; myxedema; thyrotoxicosis; bacteria and their toxins; irritable colon syndrome; diverticular disease; diabetes mellitus, progressive systemic sclerosis; idiopathic pseudo-obstruction; and ulcerative colitis.

In addition to providing a diagnostic tool for intestinal motility disease, the method of the present invention can be adopted to monitor the effectiveness of treatment of intestinal motility disease. In the method of monitoring treatment, the transit time is measured as described above. For example, a dose of the $^{13}C$ labeled material is given to the individual as part of the diagnostic regimen, respiratory gas is collected over time and the amount of labeled $CO_2$ in the respiratory gas is measured. Next the subject undergoes treatment. The treatment can involve changes in the diet, administration of a drug or other alternative treatments. After treatment, the transit time is remeasured as described above and compared with the original measurement to monitor the progression of the treatment. The remeasurement can be done daily if desired.

A further use of the present invention is a method for examining the effect of drugs or diet intake on gastrointestinal tract motility. In measuring the effect of drugs or diet on gastrointestinal tract motility, the transit time is first measured as described above. Next the drug is orally administered or the diet is altered. Then the transit time is remeasured. Changes in the gastrointestinal motility can thus be observed.

EXAMPLE 1

Synthesis of Glycosyl Ureides

Lactose-$^{13}C$-ureide and 1-$^{13}C$-lactose ureide were synthesized according to methods known in the literature. In the synthesis, lactose monohydrate and urea were used. The enrichment was $^{13}C$ urea 99 atom % $^{13}C$ and 1-$^{13}C$ lactose 60 atom % $^{13}C$ were used. The molecular structure of the $^{13}C$ lactose ureides and the putative degradation enzymes involved are shown in FIG. 1.

Arabinose-$^{13}C$-ureide and diarabinose-$^{13}C$-ureide synthesis were performed according to methods known in the literature. D-arabinose and $^{13}C$ urea were used as substrates.

Cellobiose-$^{13}C$-ureide was produced by dissolving 15 grams of D-cellobiose and 5.26 grams $^{13}C$-urea in 22 ml of boiling water. After the mixture was cooled to room temperature, the pH was adjusted to 3.0 by adding 0.44 ml of 10N HCl. The mixture was then heated in a water bath at 45° C. for 12 days. D-cellobiose-$^{13}C$-ureide began to crystallize after ethanol was added at a 1:5 ratio, and the solution was cooled to 4° C. and seeded with some cellobiose crystals. A 39% yield (6 g) was obtained. All the substrates were re-crystallized three times from hot water and ethanol.

The purity of all the synthesized products was determined by thin layer chromatography using 2-propanol-/ethyl acetate/$H_2O$ (45/20/10) as a solvent system. Compounds were visualized by staining with a mixture of p-anisaldehyde/concentrated $H_2SO_4$/ethanol (1/1/18). Lactose ureides produce blue/green spots; arabinose ureide produced green spots; and cellobiose ureides produced blue spots.

EXAMPLE 2

Glycosyl Ureide Loading Tests

In the loading tests described herein, labeled glycosyl ureides were given as an oral dose equivalent to 160 mg urea dissolved in 100 milliliters of water on separate days after the morning meal. Breath samples were collected and stored in Vacutainers ® at 30 and 15 minutes and immediately before ingestion of the test substance. Samples were collected at 0, 30, 60 minutes and at hourly intervals for 15 hours after the bolus ingestion. Urine samples were collected concurrently at one hour intervals. Twenty milliliters of each sample was lyophilized, a 3 to 4 mg aliquot of the dry matter was combusted in evacuated quart tubes at 800° C., and the cumulative urinary $^{13}C$ excretion was calculated. $^{13}C/^{12}C$ isotopic abundance of respiratory $CO_2$ and $CO_2$ produced by combustion was determined by an automated inlet gas isotope ratio mass spectrometer.

To evaluate potential competitive absorption of lactose and lactose ureide the lactose-$^{13}C$-ureide test was repeated with the simultaneous ingestion of 25 g. lactose.

EXAMPLE 3

Loading Test Results

Figure 2:
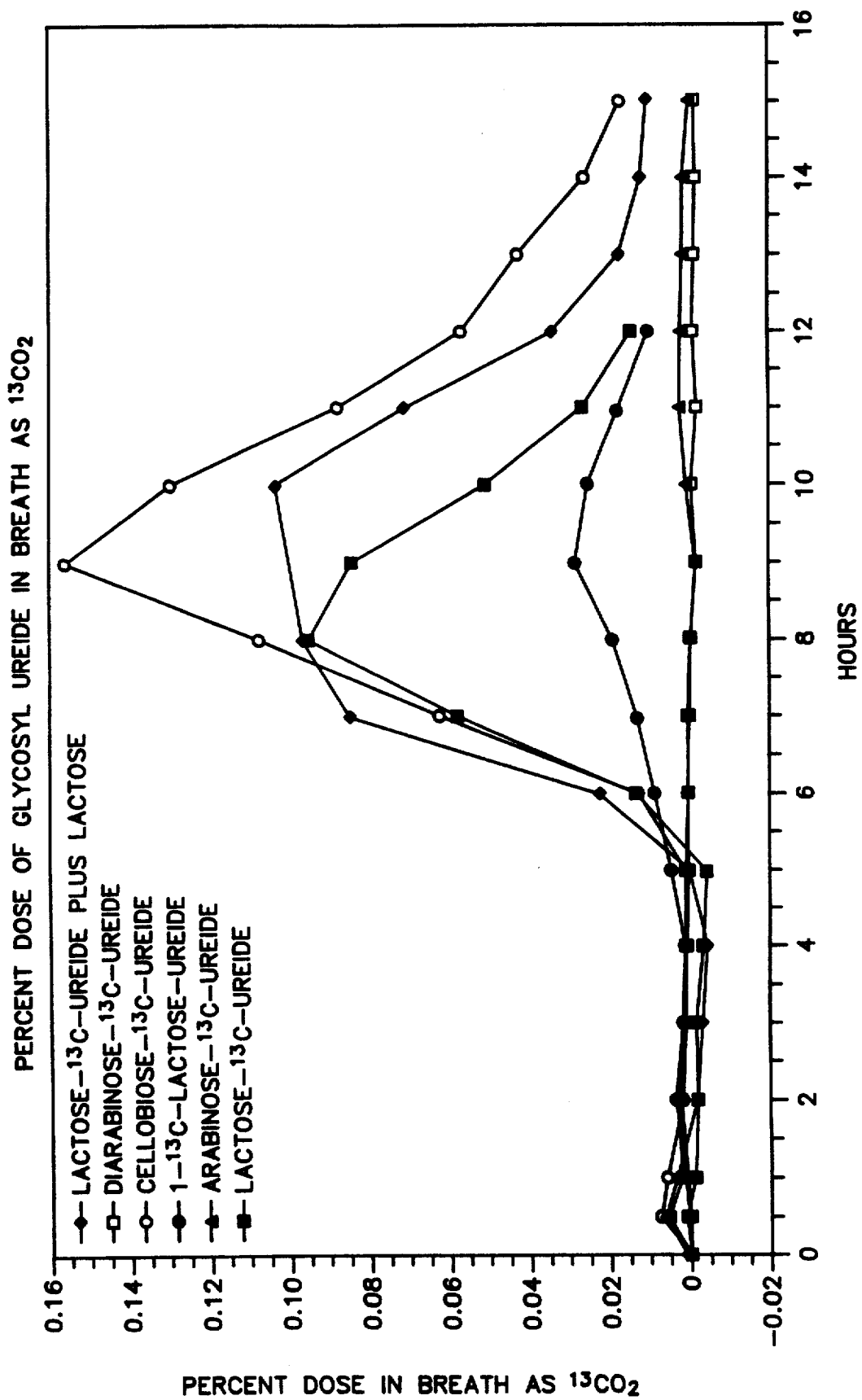
FIG. 2 shows the recovery of $^{13}CO_2$ in breath after the bolus ingestion of cellobiose-$^{13}C$-ureide (○), lactose-$^{13}C$-ureide plus lactose (◆), lactose-$^{13}C$-ureide (■), 1-$^{13}C$-lactose ureide (●), arabinose-$^{13}C$-ureide (▲), and diarabinose-$^{13}C$-ureide (□).

As seen in FIG. 2, peak values of enrichment were reached at about eight hours. The initial $^{13}CO_2$ rise was detected at about 5 to 6 hours after ingestion of the glycosyl-$^{13}C$-ureides. The $^{13}C$ abundance returned to base line values after about 15 hours. This onset of $^{13}C$ enrichment in the breath $CO_2$ samples is consistent with the transit time from the stomach to the terminal ileum. The subsequent evolution reflected the bacterial degradation of the substrate during its passage through the colon. $^{13}CO_2$ excretion in breath was calculated to be 20.2% of the ingested tracer dose (Table 1).

TABLE 1

List of glycosyl-ureides and the cumulative percent dose recovered from urine after 780 minutes and respiration after 720 minutes.

| Substrate | Cumulative percent dose | |
|---|---|---|
| | Urine | Breath |
| Cellobiose-$^{13}C$-ureide | 12.2 | 35.15 |
| Lactose-$^{13}C$-ureide plus lactose | 9.3 | 27.74 |
| Lactose-$^{13}C$-ureide | 8.5 | 20.15 |
| 1-$^{13}C$-Lactose-ureide | 7.1 | 7.45 |
| Arabinose-$^{13}C$-ureide | 7.2 | 0.83 |
| Diarabinose-$^{13}C$-ureide | 1.1 | 0.34 |

Urinary excretion of the labeled compounds occur within 1 to 2 hours after ingestion and indicate early absorption of the tracer from the upper small intestine. Urinary excretion reaches maximum level after 6 to 8 hours and was still detectable after 15 hours. The 15-hour cumulative urinary $^{13}C$ excretion after the administration of lactose-$^{13}C$-ureide was 8.5% of the tracer dose (Table 1). Administration of an additional 25 grams of lactose caused an intensification of the cumulative $^{13}CO_2$ exhalation by 27.7% but no simultaneous reduction of the urinary tracer excretion (FIG. 2 and Table 1).

Figure 3:
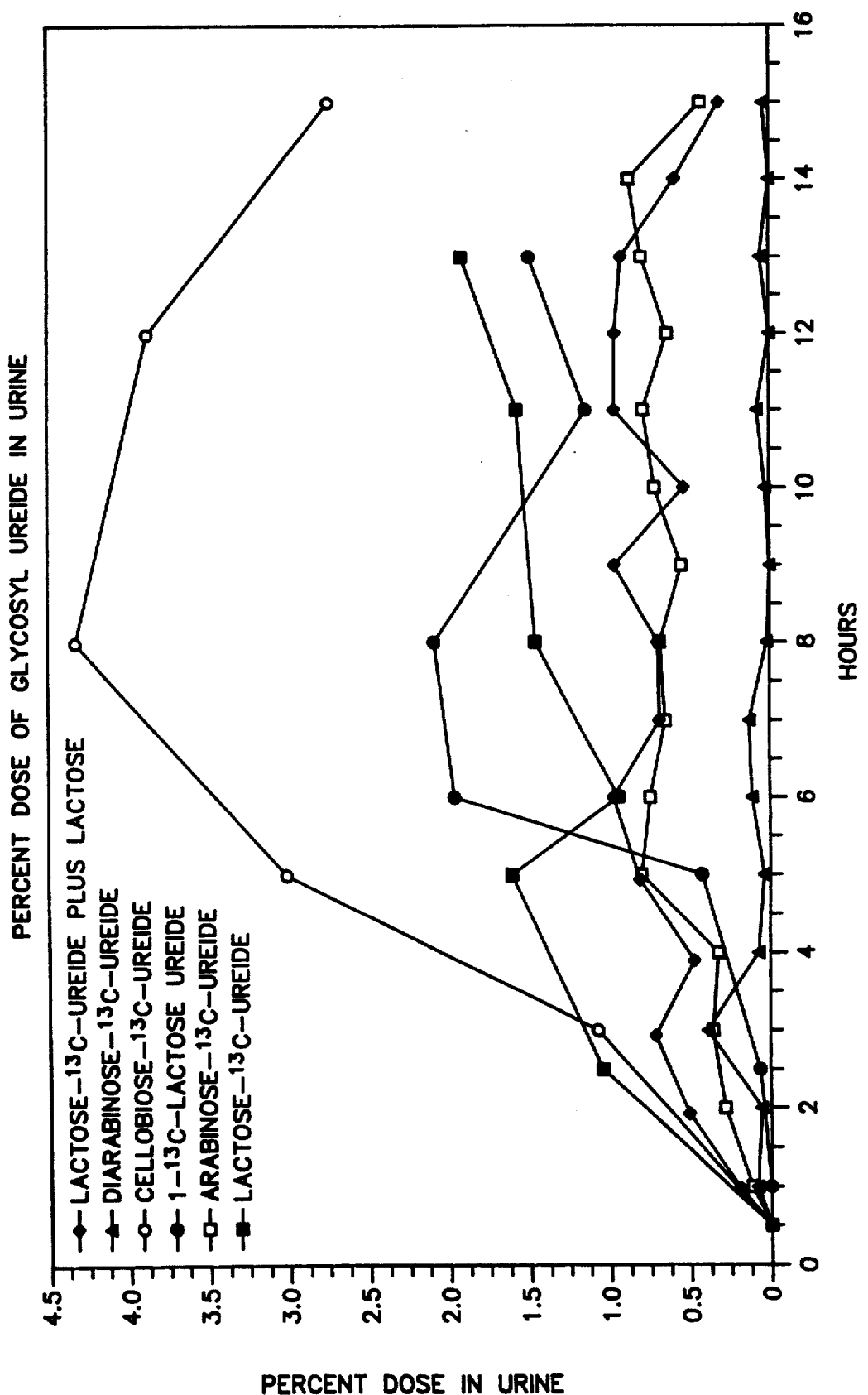
FIG. 3 shows recovery of $^{13}C$ in urine after the bolus ingestion of cellobiose-$^{13}C$-ureide (○), lactose-$^{13}C$-ureide plus lactose (◆), lactose-$^{13}C$-ureide (■), 1-$^{13}C$-lactose ureide (●), arabinose-$^{13}C$-ureide (□), and diarabinose-$^{13}C$-ureide (▲).

Breath $^{13}CO_2$ enrichment after the administration of 1-$^{13}C$ lactose ureide was somewhat less than that observed for lactose-$^{13}C$-ureide. The finding was consistent with the lower $^{13}C$ enrichment of the 1-$^{13}C$ lactose ureide used in the test. The lower enrichment also resulted from the entry of the glucose released by bacterial degradation into its metabolic pathways. Urinary $^{13}C$ excretion started one hour after the dose was administered and reached its peak between five and eight hours (FIG. 3). The renal excretion of $^{13}C$ label provided proof of the resistance of the glucose-urea linkage to endogenous metabolism.

Figure 4:
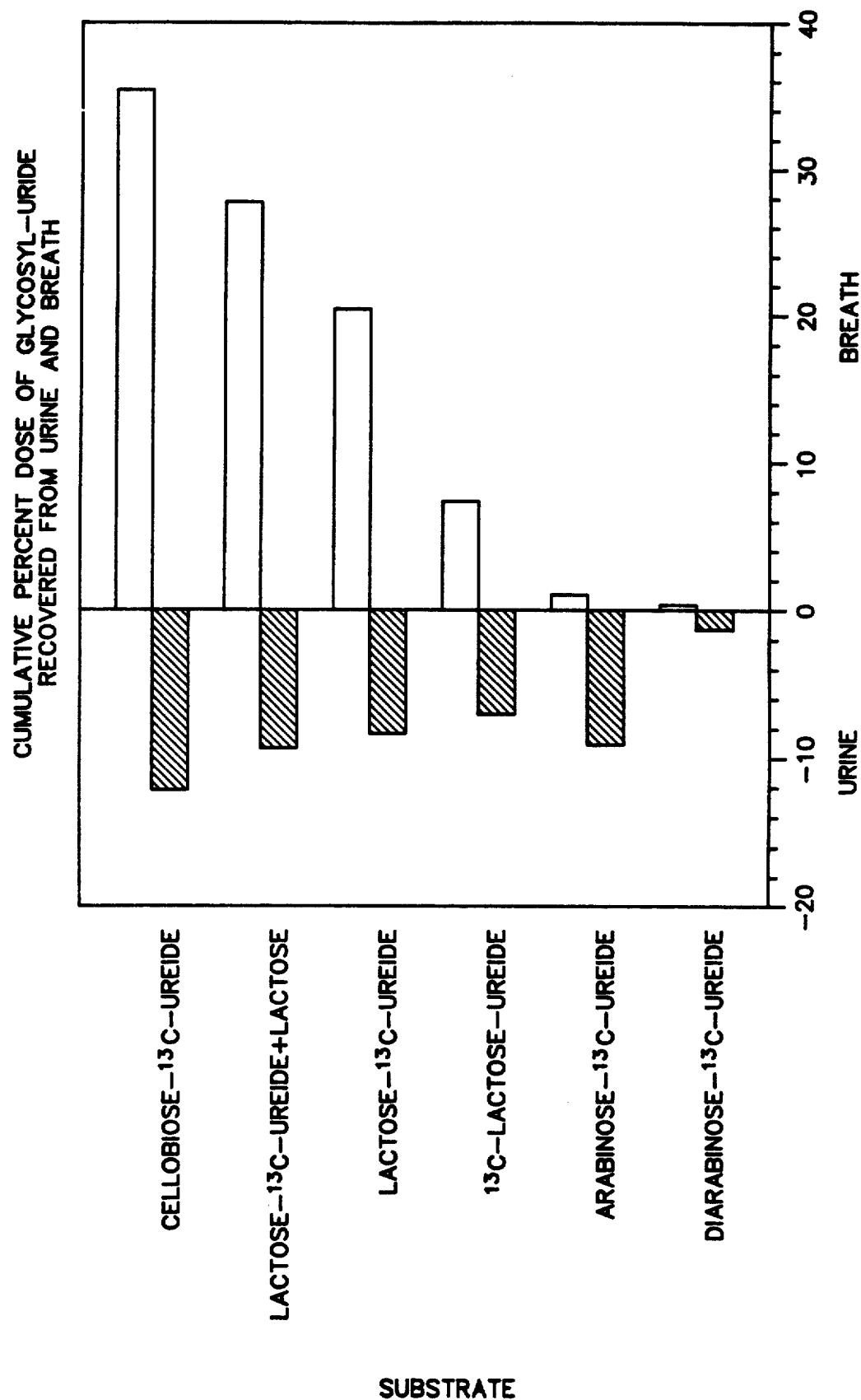
FIG. 4 is a bar graph displaying the cumulative percentage dose of each glycosyl ureide recovered from urine and breath.

Neither arabinose-$^{13}C$-ureide nor diarabinose-$^{13}C$-ureide yielded a breath test signal (FIGS. 2 and 4). Cumulative urinary $^{13}C$ excretion after ingestion of the arabinose-$^{13}C$-ureide bolus was of the same magnitude as that seen after the ingestion of lactose-$^{13}C$-ureide. Diarabinose-$^{13}C$-ureide, however, was excreted only in very small amounts, indicative of low absorption as well as resistance to the microbial breakdown of this substrate (FIGS. 3 and 4). Of all the glycosyl ureides administered, cellobiose-$^{13}C$-ureide resulted in the highest $^{13}CO_2$ enrichment in the breath (FIGS. 2 and 4).

The absorption of lactose ureides labeled with $^{13}C$ appeared to be delayed, making them suitable markers for colonic microflora. As seen with lactose-$^{13}C$-ureide, approximately 9% of the tracer substance was absorbed, and as shown by thin layer chromatography, it was excreted as glucose ureide. When additional lactose was administered with lactose-$^{13}C$-ureide, a distinct increase was observed in cumulative breath $^{13}CO_2$ (FIG. 2). This increase may indicate prolonged substrate presentation to the colon, as a consequence of competitive bacterial substrate degradation, but we cannot discount enhanced bacterial degradation of the tracer substance. The kinetics of urinary $^{13}C$ excretion indicated no evidence of competitive inhibition of the $^{13}C$-lactose ureide absorption by lactose.

The glucose ureide is absorbed and excreted in the urine in unchanged form, as shown with 1-$^{13}C$-lactose ureide (FIG. 3), or further split by colonic bacteria. There is no evidence for intermediary metabolism of the glucose ureide residue which could falsify the breath test signal. Arabinose is known to be poorly absorbed. For this reason, arabinose-$^{13}$C-ureide and diarabinose $^{13}$C-ureide were tested. Both substrates failed, however, to cause an enrichment in the breath $^{13}CO_2$ samples, apparently because both substrates resisted bacterial degradation. Cumulative urinary $^{13}$C excretion after the arabinose-$^{13}$C-ureide bolus ingestion was in the same range as the corresponding lactose-$^{13}$C-ureide excretion. In contract, diarabinose-$^{13}$C-ureide absorption was very low (Table 1).

Cellobiose-$^{13}$C-ureide appeared to be another suitable tracer substance in this series. In accord with the results derived from the lactose-$^{13}$C-ureide breath test, the stomach to cecum transit time measured with cellobiose-$^{13}$C-ureide was 5 to 6 hours. The following 10 hours in which the $^{13}CO_2$-abundance could be detected in breath represented continuous bacterial consumption of the tracer substance during colonic passage. Complete consumption of the substrate would have resulted in $^{13}CO_2$ breath values that approached baseline values.

EXAMPLE 4

Effect of Drugs on Gastrointestinal Motility

Figure 5:
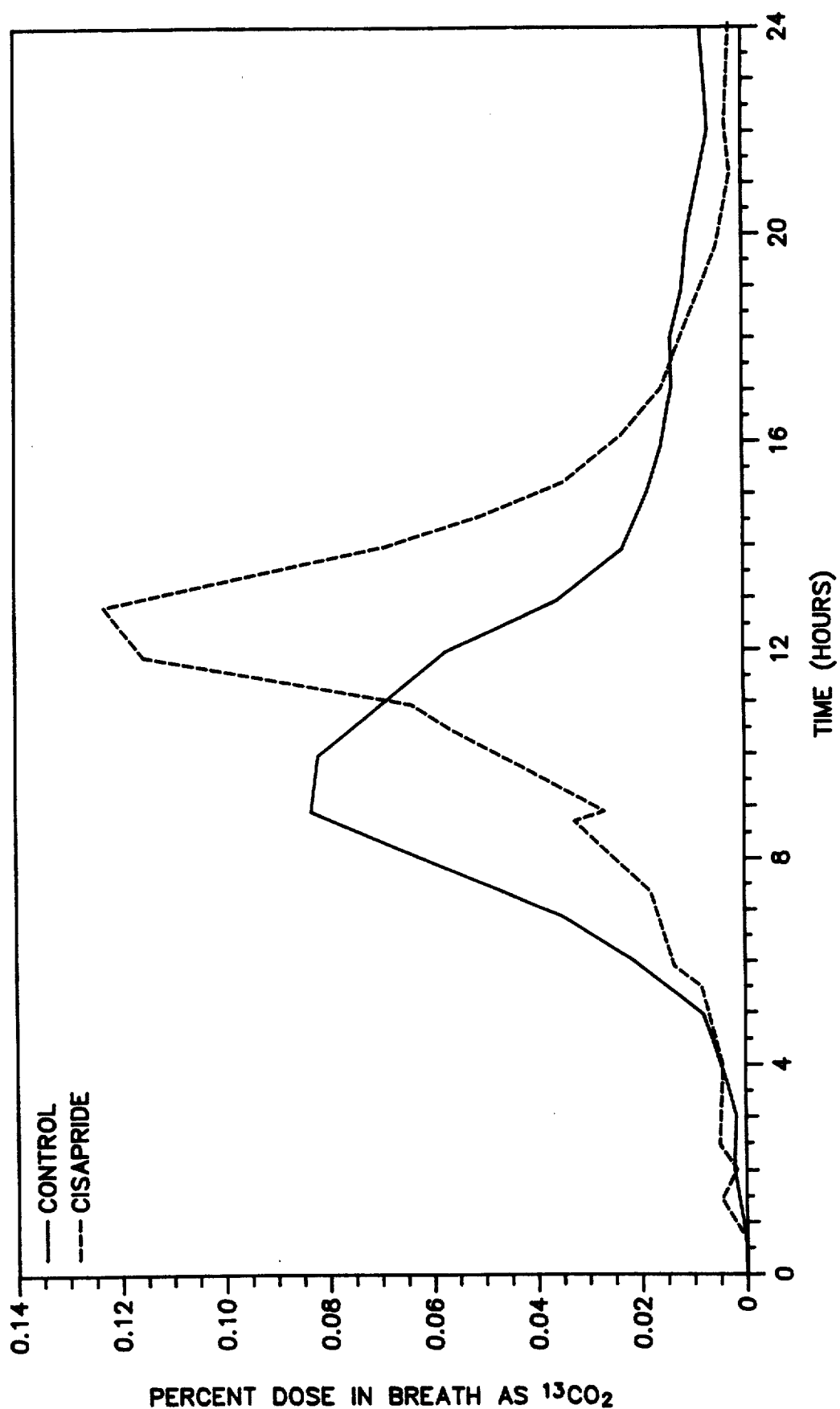
FIG. 5 shows the effect on gastrointestinal motility of the drug Cisapride. The results from the control experiment are displayed as a solid line and the results after Cisapride treatment in the same subject are displayed as a dotted line.
Figure 7:
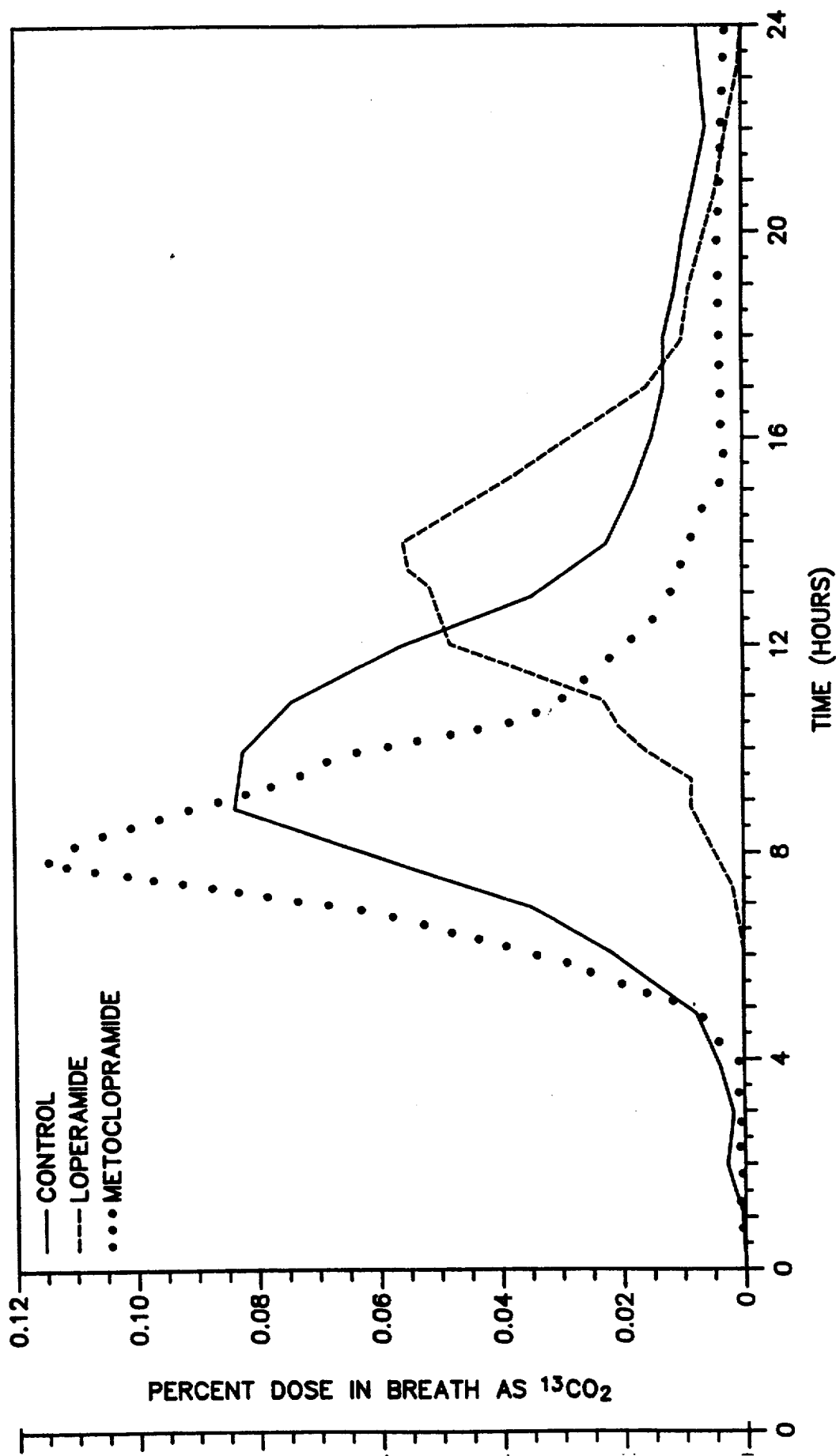
FIG. 7 shows the action of drugs on the motility of the gastrointestinal tract. The solid line represents the control, the large dashed line represents treatment with Loperamide and the short dashed line represents treatment with Metoclopramide.
Figure 8:
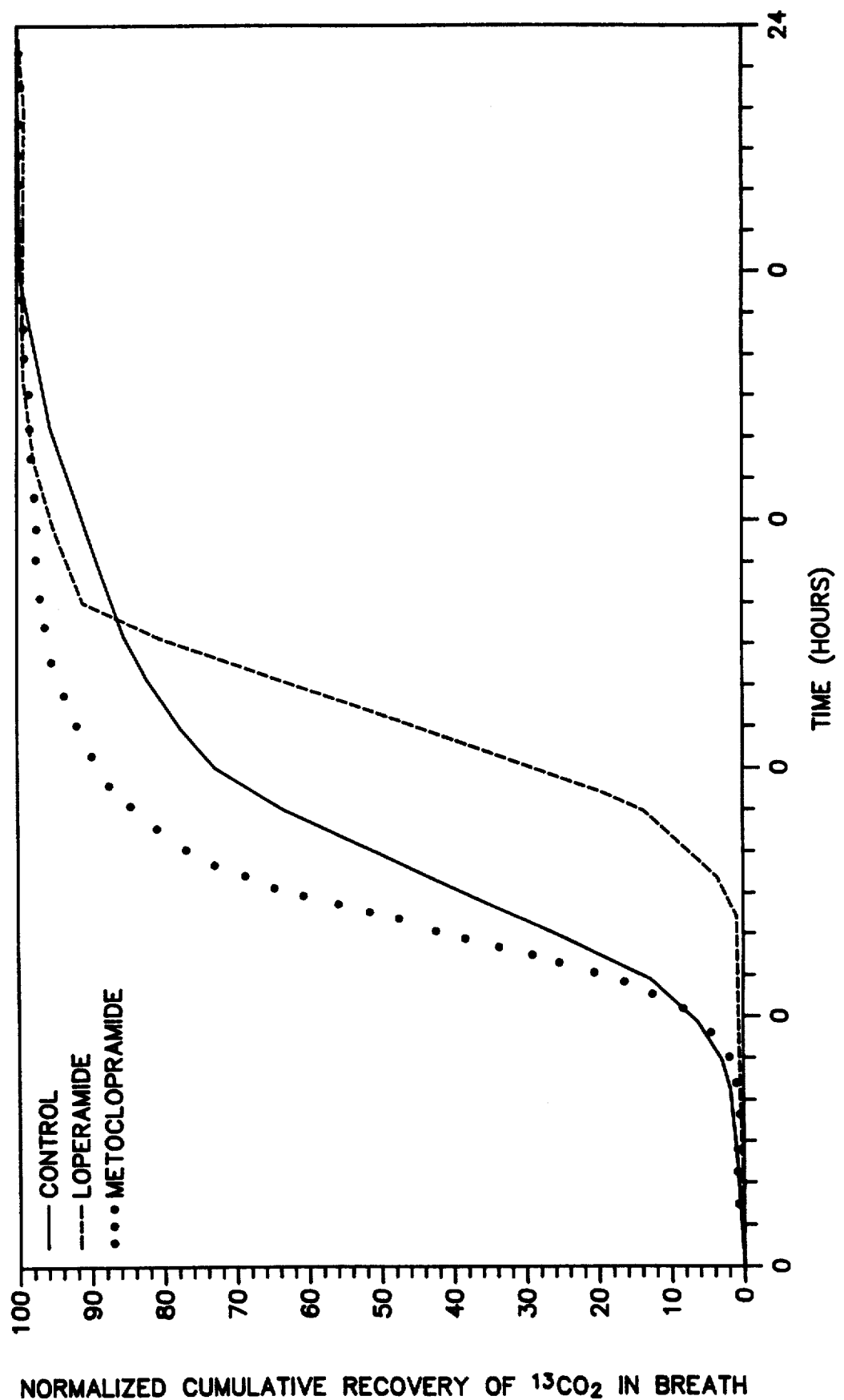
FIG. 8 shows the normalized cumulative recovery of labeled $^{13}CO_2$ in breath from control subject (solid line), Loperamide-treated subject (large dashed line) and Metoclopramide-treated subject (small dashed line).

To demonstrate the effects of drugs on gastrointestinal motility, the transmit time assay was used to measure the change in gastrointestinal motility after treatment with drugs. In this example, the baseline gastrointestinal motility was initially measured as described above. Then the subject was given a dose of 16 mg of Loperamide and again the transit time was measured. In a separate experiment the baseline motility was initially measured and the subject was given a dose of 10 mg of Metoclopramide and the transit time measured. As seen in FIGS. 7 and 8, the drugs had a significant effect on the mean transit time through the intestine. Loperamide, as expected, shows a decrease in the transit time through the gastrointestinal tract (slowing the motility), whereas Metoclopramide shows an increased transit time through the gut (increasing the motility). In an additional experiment, the effect of Cisapride on transit time was measured. Surprisingly, the Cisapride increased the transit time seen in the gastrointestinal tract (FIG. 5).

EXAMPLE 5

Control Test

Figure 6:
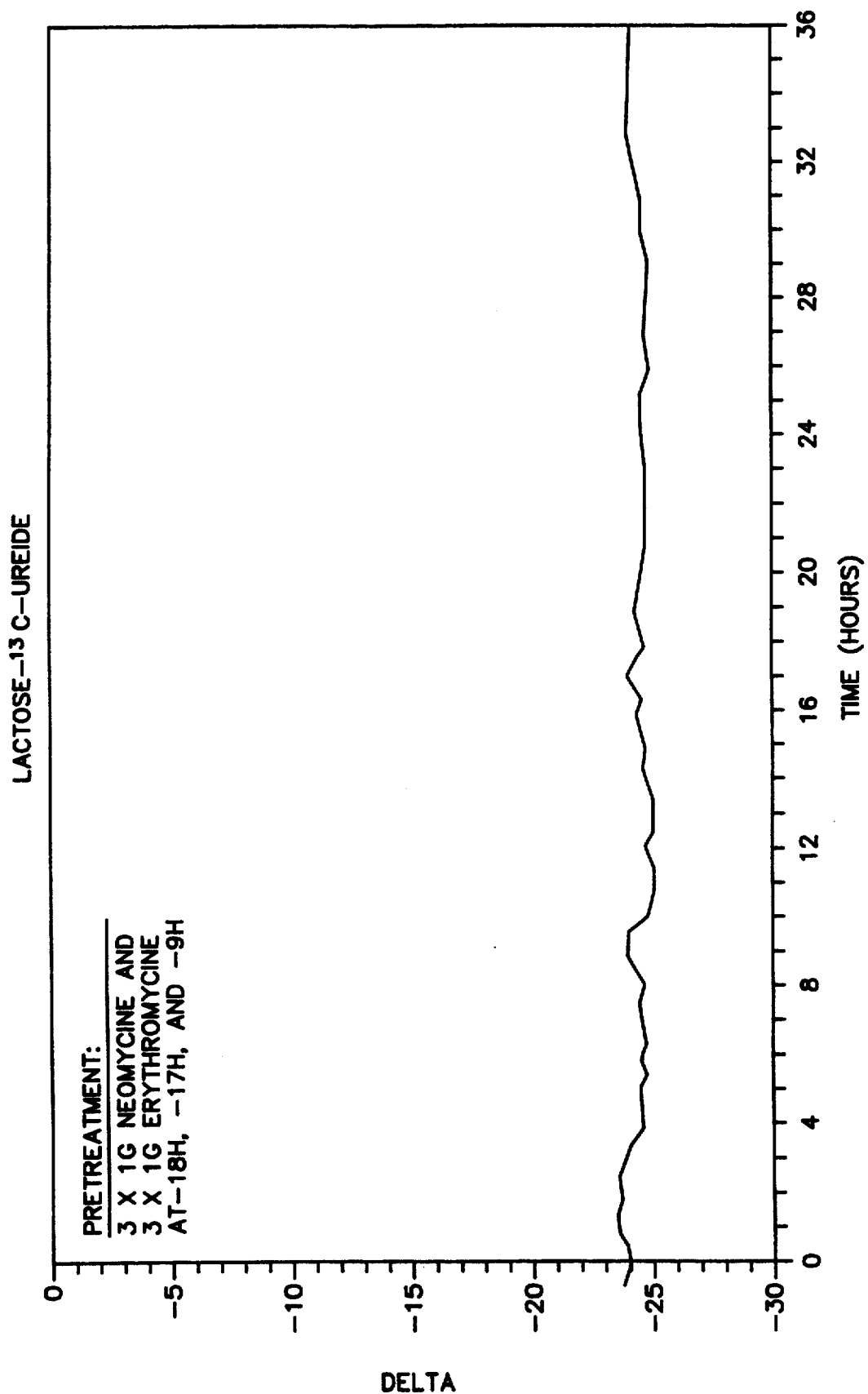
FIG. 6 shows the lack of degradation of lactose-$^{13}C$-ureide in a subject pretreated with Neomycine and Erythromycine.

To demonstrate that the assay was measuring bacterial degradation in the gastrointestinal tract rather than metabolism, a subject was pretreated with three doses of one gram each of Neomycine and three doses of one gram each of Erythromycine at −18, −17 and −9 hours prior to administration of the test dose of glycosyl ureides. As seen in FIG. 6, pretreatment with these drugs killed the bacteria and resulted in no measurable detection of the $^{13}CO_2$ after the administration of a lactose-$^{13}$C-ureide dose.

One skilled in the art will readily appreciate that the present invention is well adapted to carry out the objects and obtain the ends and advantages mentioned, as well as those inherent therein. The methods, procedures and techniques described herein are presently representative of the preferred embodiments, are intended to be exemplary and are not intended as limitations on the scope. Changes therein and other uses which are encompassed within the spirit of the invention or defined by the scope of the appended claims will occur to those skilled in the art.

What is claimed is:

1. A non-invasive method for determining intestinal transit time, comprising the steps of:
    administering an oral testing dose of labeled glycosyl ureide to a subject to be tested;
    sampling respiratory gas over time from said subject; and
    measuring the amount of label in said respiratory gas.

2. The method of claim 1 wherein the labeled glycosyl ureide is selected from the group consisting of lactose-$^{13}$C-ureide, cellobiose-$^{13}$C-ureide and 1-$^{13}$C-lactose ureide; and $^{13}CO_2$ is measured in said respiratory gas.

3. A method of diagnosing intestinal motility disease, comprising the steps of:
    performing the non-invasive test of claim 1 to determine the transit time; and
    comparing said transit time with normal transit time.

4. A method of monitoring the effectiveness of treatment of intestinal motility disease, comprising the steps of:
    measuring the transit time by the method of claim 1;
    administering the treatment; and
    repeating said measuring the transit time step.

5. A method for measuring the effect of drugs or diet on gastrointestinal tract motility, comprising the steps of:
    measuring the transit time by the method of claim 1;
    altering the diet or orally administering the drug to be tested; and
    repeating said measuring the transit time step.

6. The method of claim 1, wherein the dose of labeled glycosyl ureide is 10 to 20 mg/kg.

7. The method of claim 1, wherein the oral dose of label is equivalent to 1 to 5 mg/kg of urea.

8. The method of claim 7, wherein the label is equivalent to 2.5 mg/kg of urea.

9. The method of claim 1, wherein the respiratory gas is sampled at half-hour intervals, up to 24 hours.

10. A non-invasive method for determining intestinal transit time, comprising the steps of:
    administering an oral dose of labeled glycosyl ureide of 10 to 20 mg/kg of body weight to a subject to be tested;
    sampling respiratory gas by collecting said gas at 30 minutes, 60 minutes and every hour thereafter up to 24 hours after administering the labeled glycosyl ureide; and
    measuring the amount of label in said samples.

11. The method of claim 10 wherein the glycosyl ureide is selected from the group consisting of lactose-$^{13}$C-ureide, cellobiose-$^{13}$C-ureide and 1-$^{13}$C-lactose ureide; and $^{13}CO_2$ is measured in said respiratory gas.

* * * * *